United States Patent [19]
Roberts et al.

[11] Patent Number: 6,163,723
[45] Date of Patent: Dec. 19, 2000

[54] CIRCUIT AND METHOD FOR IMPLANTABLE DUAL SENSOR MEDICAL ELECTRICAL LEAD

[75] Inventors: Jonathan P. Roberts, Shoreview; Glenn M. Roline, Anoka; Brian B. Lee, Golden Valley, all of Minn.

[73] Assignee: Medtronic, Inc., Minneapolis, Minn.

[21] Appl. No.: 09/177,540

[22] Filed: Oct. 22, 1998

[51] Int. Cl.$^7$ .................................................. A61N 1/365
[52] U.S. Cl. .............................................................. 607/18
[58] Field of Search ................................. 607/2, 9, 16, 18

[56] References Cited

U.S. PATENT DOCUMENTS

| | | |
|---|---|---|
| H1114 | 12/1992 | Schweitzer et al. . |
| 3,746,087 | 7/1973 | Lavering et al. . |
| 3,847,483 | 11/1974 | Shaw et al. . |
| 4,114,604 | 9/1978 | Shaw et al. . |
| 4,202,339 | 5/1980 | Wirtzfeld et al. . |
| 4,399,820 | 8/1983 | Wirtzfeld et al. . |
| 4,407,296 | 10/1983 | Anderson . |
| 4,421,386 | 12/1983 | Podgorski . |
| 4,444,498 | 4/1984 | Heinemann . |
| 4,467,807 | 8/1984 | Bornzin . |
| 4,523,279 | 6/1985 | Sperinde et al. . |
| 4,554,927 | 11/1985 | Fussell . |
| 4,623,248 | 11/1986 | Sperinde . |
| 4,651,741 | 3/1987 | Passafaro . |
| 4,697,593 | 10/1987 | Evans et al. . |
| 4,727,879 | 3/1988 | Liess et al. . |
| 4,730,389 | 3/1988 | Baudino et al. . |
| 4,730,622 | 3/1988 | Cohen . |
| 4,750,495 | 6/1988 | Moore et al. . |
| 4,791,935 | 12/1988 | Baudino et al. . |
| 4,807,629 | 2/1989 | Baudino et al. . |
| 4,807,632 | 2/1989 | Liess et al. . |
| 4,813,421 | 3/1989 | Baudino et al. . |
| 4,815,469 | 3/1989 | Cohen et al. . |
| 4,827,933 | 5/1989 | Koning et al. . |
| 4,830,488 | 5/1989 | Heinze et al. . |

(List continued on next page.)

FOREIGN PATENT DOCUMENTS

| | | |
|---|---|---|
| WO 80/01620 | 8/1980 | WIPO . |
| WO 94/13200 | 6/1994 | WIPO . |

OTHER PUBLICATIONS

Hin–Leung Chau, Member, IEEE, and Kensall D. Wise, Fellow, IEEE, "An Ultraminiature Solid–State Pressure Sensor for a Cardiovascular Catheter," IEEE Trans. Electron Devices, vol. 35, No. 12, pp. 2355–2362, Dec. 1988.

"Capacitive Transducers," Capacitive Gaging System, courtesy of Lion Precision Corp., Newton, Mass. Section 4.1, in part, is from Harry E. Thomas *Handbook of Biomeical Instrumentation and Measurement*, Reston Publishing Co., Reston, Va., 1974, p. 12.

*Primary Examiner*—George R. Evanisko
*Attorney, Agent, or Firm*—Thomas F. Woods; Girma Wolde-Michael; Harold R. Patton

[57] ABSTRACT

An implantable dual transducer apparatus for use with an implantable medical device and control method are disclosed. The dual transducer assembly includes two physiologic sensors coupled to the medical device via a pair of lead conductors. Switching circuitry is controlled by the medical device to selectively activate and deactivate the two physiologic sensors by application of a supply voltage of an appropriate polarity. Each sensor of the dual transducer assembly is connected to the pair of lead conductors through a respective power switch. In response to the polarity of the supply voltage applied to the lead conductors, the power switches activate or deactivate their respective sensor in an alternating manner. Selective activation of one of the sensor while concurrently deactivating the other sensor of the dual transducer assembly provides for reduced power consumption and reliable communication of sensor data and other information transmitted over the pair of lead conductors. The power switches may be constructed using diodes, including discrete or substrate diodes, or transistors, such as n-channel and p-channel transistors. A wide variety of physiologic sensors may be incorporated into the dual transducer assembly.

28 Claims, 12 Drawing Sheets

U.S. PATENT DOCUMENTS

| | | |
|---|---|---|
| 4,877,032 | 10/1989 | Heinze et al. ............................. 607/2 |
| 4,903,701 | 2/1990 | Moore et al. . |
| 4,967,755 | 11/1990 | Pohndorf . |
| 5,005,573 | 4/1991 | Buchanan . |
| 5,040,538 | 8/1991 | Mortazavi . |
| 5,052,388 | 10/1991 | Sivula et al. . |
| 5,058,586 | 10/1991 | Heinze . |
| 5,067,960 | 11/1991 | Grandjean . |
| 5,113,862 | 5/1992 | Mortazavi . |
| 5,113,868 | 5/1992 | Wise et al. . |
| 5,176,138 | 1/1993 | Thacker . |
| 5,199,428 | 4/1993 | Obel et al. . |
| 5,267,564 | 12/1993 | Barcel et al. . |
| 5,275,171 | 1/1994 | Barcel . |
| 5,312,454 | 5/1994 | Roline et al. . |
| 5,324,326 | 6/1994 | Lubin . |
| 5,329,922 | 7/1994 | Atlee, III . |
| 5,342,406 | 8/1994 | Thompson . |
| 5,358,519 | 10/1994 | Grandjean . |
| 5,377,524 | 1/1995 | Wise et al. . |
| 5,411,532 | 5/1995 | Mortazavi . |
| 5,438,987 | 8/1995 | Thacker et al. . |
| 5,490,323 | 2/1996 | Thacker et al. . |
| 5,535,752 | 7/1996 | Halperin et al. . |
| 5,556,421 | 9/1996 | Prutchi et al. . |
| 5,564,434 | 10/1996 | Halperin et al. . |
| 5,593,430 | 1/1997 | Renger . |
| 5,601,611 | 2/1997 | Fayram et al. . |
| 5,743,267 | 4/1998 | Nikolic et al. . |
| 5,758,652 | 6/1998 | Nikolic et al. . |
| 5,766,228 | 6/1998 | Bonnet et al. ............................. 607/16 |
| 5,788,647 | 8/1998 | Eggers . |
| 6,002,963 | 12/1999 | Mouchawar et al. ..................... 607/18 |
| B1 4,467,807 | 6/1992 | Bornzin . |

CIRCUIT AND METHOD FOR IMPLANTABLE DUAL SENSOR MEDICAL ELECTRICAL LEAD

FIELD OF THE INVENTION

The present invention relates generally to implantable physiologic sensors. More particularly, the present invention pertains to an implantable dual transducer assembly and method for controlling same.

BACKGROUND OF THE INVENTION

Various medical devices have been developed to receive information from one or more physiologic sensors or transducers. A typical physiologic sensor converts a measurable parameter of the human body, such as blood pressure, temperature or oxygen saturation for example, into corresponding electrical signals. A conventional approach to attaching a physiologic sensor to a multiple conductor lead extending from an implantable medical device involves connecting the sensor to at least two conductors provided in the lead.

Connecting two physiologic sensors to an implantable medical device in a conventional manner typically involves connecting the medical device to two multiple conductor leads, with a dedicated lead connected to each of the two sensors. The additional number of leads and associated connection hardware generally complicates the design of the leads and medical device electronics, increases power consumption and the cost of the device, and reduces overall device reliability.

An improved approach to connecting a medical device to two or more physiologic sensors is disclosed in U.S. Pat. No. 5,593,430 issued to Renger. The disclosed approach involves connecting each of the sensors in parallel to a two conductor lead. Although the number of conductor leads may be minimized to two conductors for a multiple sensor implementation, the approach disclosed in U.S. Pat. No. 5,593,430 requires deployment of a relatively complex bus protocol, such as one requiring time division multiplexing, frequency division multiplexing, or a sensor addressing scheme for coordinating bus arbitration.

Moreover, the approach disclosed in U.S. Pat. No. 5,593,430 also requires that power be applied to all sensors concurrently or removed from all sensors concurrently, even though only one of the sensors need be active or inactive during a given period of time. Assuming, arguendo, that a microprocessor bus control system, such as that disclosed in U.S. Pat. No. 5,593,430, could be used to deactivate a selected physiologic sensor, such an approach would require continuous power consumption at the sensor in order to monitor the bus for control signals transmitted by the implantable medical device. The amount of current expended by the sensor to monitor the bus would typically be on the order of a few microamps, thereby doubling the average power consumption to operate the sensor in a typical application.

Various implementations of systems for interconnecting one or more physiologic sensors with an implantable medical device are known in the art, a some examples of which may be found in the issued U.S. patents listed in Table 1 below.

TABLE 1

| Patent No. | Inventor(s) | Issue Date |
|---|---|---|
| 4,432,372 | Monroe | February 21, 1984 |
| 4,750,495 | Moore et al. | June 14, 1988 |
| 4,903,701 | Moore et al. | February 27, 1990 |
| 5,113,868 | Wise et al. | May 19, 1992 |
| 5,324,326 | Lubin | June 28, 1994 |
| 5,377,524 | Wise et al. | January 3, 1995 |
| 5,535,752 | Halpenn et al. | July 16, 1996 |
| 5,564,434 | Halpenn et al. | October 15, 1996 |
| 5,593,430 | Renger | January 14, 1997 |

All patents listed in Table 1 hereinabove are hereby incorporated by reference herein in their respective entireties. As those of ordinary skill in the art will appreciate readily upon reading the Summary of the Invention, the Detailed Description of the Various Embodiments, and the claims set forth below, many of the devices and methods disclosed in the patents of Table 1 may be modified advantageously by using the teachings of the present invention.

SUMMARY OF THE INVENTION

The present invention has certain objects. That is, various embodiments of the present invention provide solutions to one or more problems existing in the prior art with respect to implantable physiologic sensors and interconnecting such sensors with implantable medical devices. Such problems include, for example, numerous lead conductors required for interconnecting a pair of physiologic sensors, complex techniques required to effect control and communications between a pair of physiologic sensors and an implantable medical device, reduced reliability resulting from increased complexity of multiple sensor communications, control, and interfacing techniques, and high power consumption associated with concurrent operation of multiple interconnected sensors. Various embodiments of the present invention have the object of solving at least one of the foregoing problems. While some systems have been able to solve the general problem of interconnecting multiple physiologic sensors with an implantable medical device using a pair of lead conductors, such approaches have generally resulted in implementations that increase power usage and require deployment of complex addressing schemes and/or time or frequency multiplexing/demultiplexing communication schemes. It is therefore another object of the present invention to provide an improved assembly and methodology for interconnecting and controlling two physiologic sensors using a pair of lead conductors that fulfills at least one of the foregoing objects.

In comparison to known implementations of implantable multiple sensor assemblies, various embodiments of the present invention may provide one or more of the following advantages: reducing the power required by a pair of physiologic sensors that derive power from an implantable medical device; increasing the reliability of an implantable medical device system which employs a pair of physiologic sensors; interfacing different types of sensors incorporated in a dual sensor assembly with a wide variety of implantable medical devices; increasing the integrity of sensor data and control information communicated between a pair of physiologic sensors and an implantable medical device; and simplifying lead construction.

Some embodiments of the invention include one or more of the following features: a power switch coupled to a pair of physiologic sensors to selectively activate and deactivate the two sensors; two power switches each connected to a respective one of a pair of physiologic sensors to selectively activate and deactivate the two sensors; two n-channel power MOSFET switches each connected to a respective one of a pair of physiologic sensors to selectively activate and deactivate the two sensors; two p-channel power MOSFET switches each connected to a respective one of a pair of physiologic sensors to selectively activate and deactivate the two sensors; an n-channel power MOSFET switch and a p-channel MOSFET switch connected to a respective one of a pair of physiologic sensors to selectively activate and deactivate the two sensors; two diodes having opposite polarities each connected in parallel with a respective physiologic sensor such that each diode acts as a shunt to its respective sensor in response to one of a positive or negative supply voltage; a two conductor lead connecting two controllable physiologic sensor units in series; a two conductor lead connecting two controllable physiologic sensor units in parallel; and an interface circuit for interfacing a dual transducer assembly with a control unit or recovery unit of an implantable medical device.

The above summary of the present invention is not intended to describe each embodiment or every implementation of the present invention. Advantages and attainments, together with a more complete understanding of the invention, will become apparent and appreciated by referring t-o the following detailed description and claims taken in conjunction with the accompanying drawings.

Figure 1:
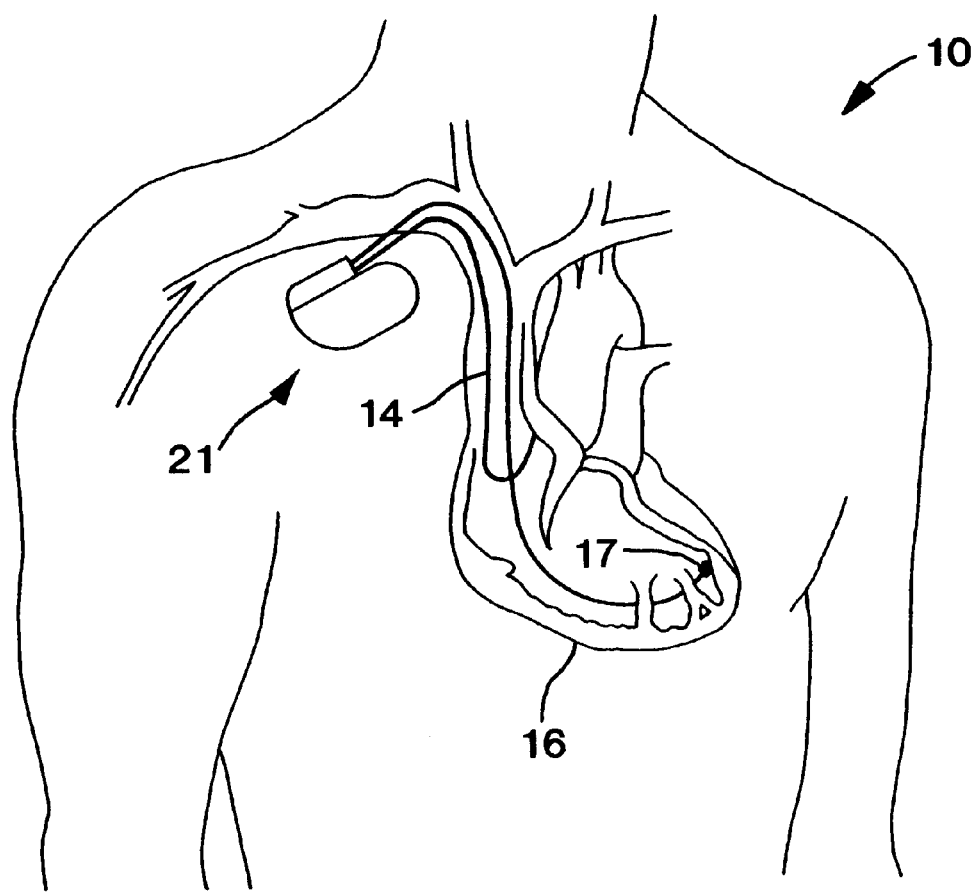
FIG. 1 shows an implantable medical device coupled to a dual transducer assembly in accordance with an embodiment of the present invention implanted in a human body.

While the invention is amenable to various modifications and alternative forms, specifics thereof have been shown by way of example in the drawings and will be described in detail hereinbelow. It is to be understood, however, that the intention is not to limit the invention to the particular embodiments described. On the contrary, the invention is intended to cover all modifications, equivalents, and alternatives falling within the spirit and scope of the invention as defined by the appended claims.

DETAILED DESCRIPTION OF THE PREFERRED EMBODIMENTS

In the following description of the preferred embodiments, references are made to the accompanying drawings which form a part hereof, and in which is shown by way of illustration, various embodiments in which the invention may be practiced. It is to be understood that other embodiments may be utilized, and structural and functional changes may be made without departing from the scope of the present invention.

U.S. patent application Ser. No. 09/182,970 filed Oct. 30, 1998 for "Multiple Sensor Assembly for Medical Electrical Lead" to Miesel et al., hereby incorporated by reference herein, in its entirety, discloses a dual sensor housing and corresponding sub-housings therefor finding particularly efficacious application in connection with the below-described invention.

Figure 3:
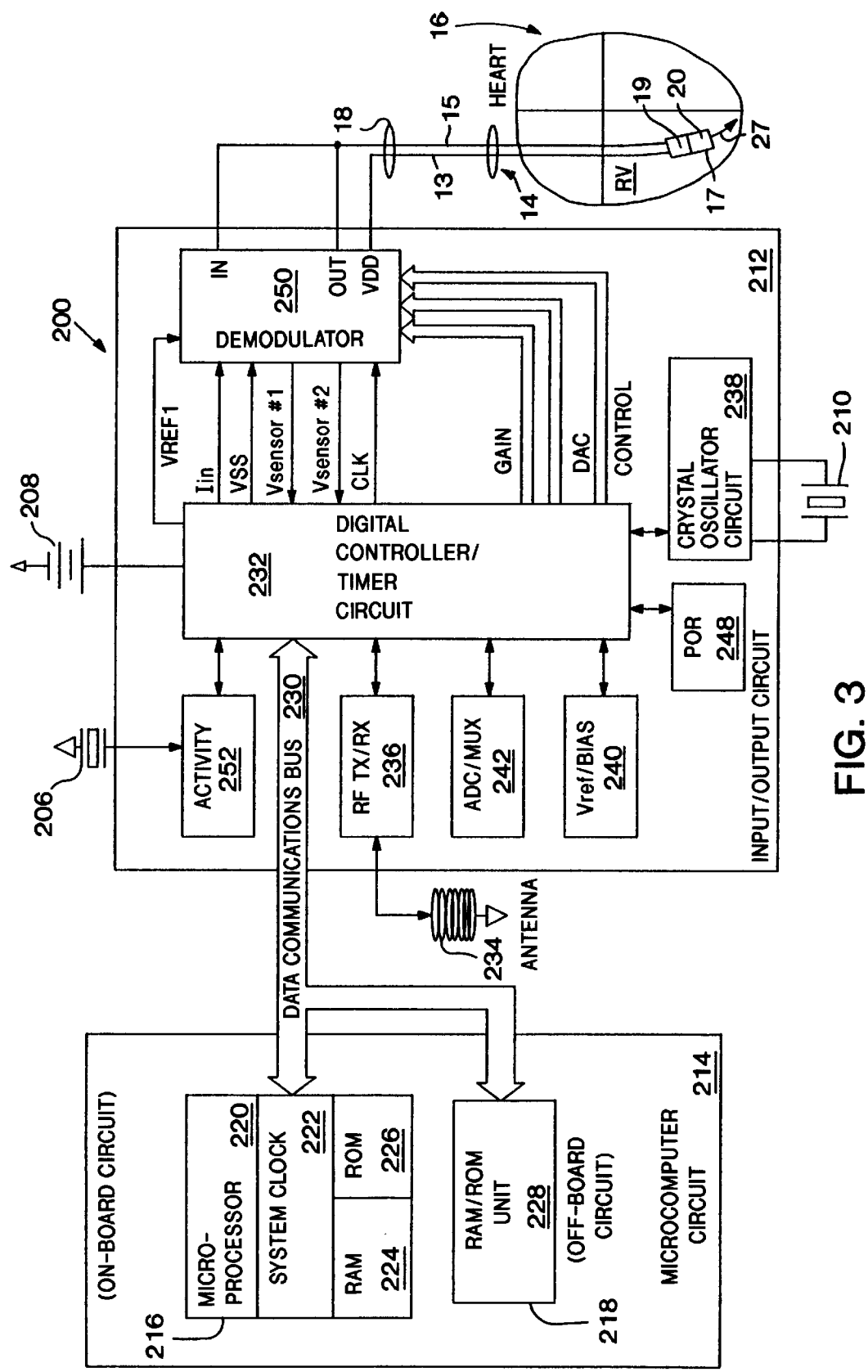
FIG. 3 shows an implantable medical device including a sensor monitor unit coupled to a dual transducer assembly in accordance with a further embodiment of the present invention.

FIG. 1 is a simplified schematic view of a medical device 21 implanted in a human body 10. A dual transducer assembly 17 according to the present invention is shown implanted in a human heart 16 and coupled to the medical device 21. The dual transducer assembly 17, as is shown in FIG. 3, includes two sensors 19, 20, each of which senses one or more physiologic parameters associated with the human heart 16. The lead 14 includes two conductors 13, 15. Each of the two sensors 19, 20 included within the dual transducer assembly 17 is coupled to one or both of the two conductors 13, 15 in either a series or parallel configuration.

The two sensors 19, 20 of the dual transducer assembly 17 are selectively and alternately activated and deactivated in a manner appropriate for a particular physiologic sensor and monitoring application. In one embodiment, power is selectively applied to one of the two sensors 19, 20 of the dual transducer assembly 17 and concurrently removed from the other one of the two sensors 19, 20, which advantageously reduces power consumption.

Controlling the application and removal of power to and from selected sensors 19, 20 of the dual transducer assembly 17 in this manner may significantly reduce the overall power requirements of the medical device 21 and extend battery life. A conventional power control approach, in contrast, is generally incapable of applying and removing power to selected sensors coupled to a two conductor lead. Rather, such prior art schemes typically require that power be applied to all sensors concurrently and removed from all sensors concurrently, even when only one of the sensors need be active or inactive during a given period of time. A system which incorporates the dual transducer assembly 17 and control methodology according to the present invention may completely disable a selected one of the two sensors 19, 20, with no need to monitor the two conductor lead or bus. In such a configuration, no increase in power consumption related to activating and deactivating the selected sensor is experienced.

Signals produced by each of the sensors 19, 20 are transmitted to the medical device 21 during the time in which a selected sensor is operational. As such, each sensor 19, 20 is afforded exclusive use of the lead conductors 13, 15 to effect communications with the medical device 21. This manner of controlling the dual transducer assembly 17 obviates the need for employing complex addressing and time or frequency modulation/demodulation techniques associated with prior art schemes that require usage of a common pair of lead conductors. The simple yet elegant methodology for controlling a dual transducer assembly 17 in accordance with the principles of the present invention provides for increased reliability and reduced power consumption, two advantages which are of particular importance in medical device applications.

In general, implantable physiologic sensors are designed to operate on the lowest amount of power possible for a given application, while retaining the ability to reliably detect and transmit the measured information. A physiologic sensor implemented in such a low power application will typically draw an average current of up to a few microamps. Some sensors, such as optical oxygen saturation sensors, have an instantaneous current draw that is much higher, such as up to several milliamps for example. However, this type of sensor is designed to be operated for short durations, such as 5 milliseconds, at and at relatively wide intervals, such as 5 seconds for example. With an average current draw of 2 milliamps when operating, and given the above timing specification, the average current draw of such a sensor would be 2 microamps. It is readily appreciated by one skilled in the art that selectively disabling the high current draw of such a sensor is necessary to achieve a low power dual sensor implementation.

In one embodiment, the two sensors 19, 20 of the dual transducer assembly 17 are selectively activated and deactivated for operation in response to variations in the polarity of a supply voltage generated by the medical device 21 and applied to the pair of conductors 13, 15. One of the two sensors 19, 20 of the dual transducer assembly 17 may be operated for a period of time similar to or different from the other sensor 19, 20. By way of example, and assuming that a pressure sensor and an oxygen saturation sensor constitute the two sensor 19, 20 of the dual transducer assembly 17, the pressure sensor 20 may be operated for a period of time during each depolarization/re-polarization cycle of the heart 16. The oxygen saturation sensor, in contrast, may be operated for a period of time during every third depolarization/re-polarization cycle of the heart 16.

It can be readily appreciated from this illustrative example that powering the oxygen sensor only when required (i.e., once every third depolarization/re-polarization cycle) can reduce the power requirement for the oxygen sensor by as much as 66 percent in comparison to a scheme which requires concurrent delivery of power to the pressure and oxygen saturation sensors. A dual transducer assembly and control methodology implemented in accordance with the principles of the present invention advantageously provides an elegant, low power, and reliable approach to selectively monitoring two or more physiologic parameters associated with a human heart 16 or other organ using only two conductors 13, 15 of a lead 14.

It will be appreciated that a dual transducer assembly 17 and control methodology according to the present invention may be implemented to operate in a unipolar mode or a bipolar mode using a two conductor lead 14 in cooperation with a wide variety of implantable medical devices. In the case where the implanted medical device 21 shown in FIG. 1 is a pacemaker, one of the two conductors 13, 15 of lead 14 is typically connected between the heart 16 from the implantable medical device 21. The lead 14, which typically includes a tine electrode, senses electrical signals attendant to the depolarization and re-polarization of the heart 16 and transmits pacing pulses for causing depolarization of cardiac tissue in the vicinity of the distal ends thereof. The medical device 21 may be an implantable cardiac pacemaker, such as those disclosed in U.S. Pat. No. 5,158,078 to Bennett et al., U.S. Pat. No. 5,312,453 to Shelton et al., or U.S. Pat. No. 5,144,949 to Olson, hereby incorporated herein by reference in their respective entireties.

The implantable medical device 21 may also be a pacemaker/cardioverter/defibrillator (PCD), one embodiment of which is further described below. The present invention may be practiced in conjunction with PCDs, such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless, or U.S. Pat. No. 4,821,723 to Baker et al., all hereby incorporated herein by reference in their respective entireties. Those devices may be employed in conjunction with the dual transducer assembly 17 of the present invention.

Alternatively, the medical device 21 may be an implantable nerve stimulator or muscle stimulator, such as those disclosed in U.S. Pat. No. 5,199,428 to Obel et al., U.S. Pat. No. 5,207,218 to Carpentier et al., or U.S. Pat. No. 5,330,507 to Schwartz, or an implantable monitoring device, such as that disclosed in U.S. Pat. No. 5,331,966 issued to Bennet et al., all of which are hereby incorporated herein by reference in their respective entireties. The present invention is believed to find wide application to any form of implantable electrical device which requires information derived from two physiologic sensors, and the present invention is believed to be particularly advantageous in those contexts where a low power consumption design is employed and desired.

In general, the implantable medical device 21 shown in FIG. 1 includes a hermetically-sealed enclosure that may include various elements, such as an electrochemical cell (e.g., a lithium battery), circuitry that controls device operations and records arrhythmic EGM episodes, telemetry transceiver antenna and circuit that receives downlinked telemetry commands from and transmits stored data in a telemetry uplink to an external programmer, in addition to other elements.

Figure 2A:
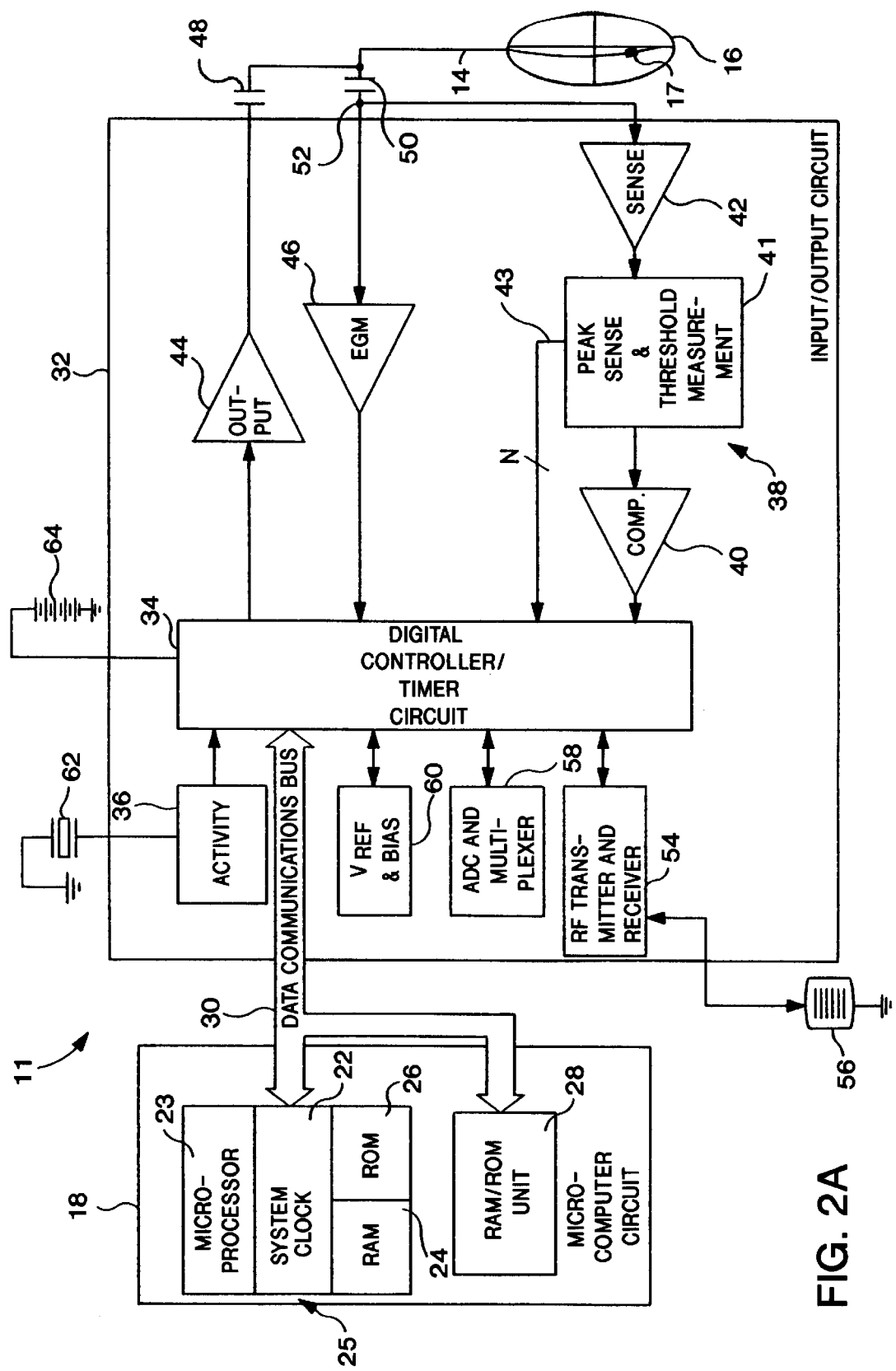
FIG. 2A shows an implantable pacemaker device coupled to a dual transducer assembly in accordance with one embodiment of the present invention.

FIG. 2A is a block diagram illustrating various components of a pacemaker 11 which represents one of many implantable medical devices that may derive physiologic information from a dual transducer assembly 17 of the present invention. In one embodiment, the pacemaker 11 is programmable by means of an external programming unit (not shown). One such programmer suitable for the purposes of the present invention is the commercially available Medtronic Model 9790 programmer. The programmer is a microprocessor device which provides a series of encoded signals to pacemaker 11 by means of a programming head which transmits radio frequency (RF) encoded signals to pacemaker 11 according to a telemetry system such as that described in U.S. Pat. No. 5,312,453 to Wyborny et al., the disclosure of which is hereby incorporated by reference herein in its entirety. It is to be understood, however, that the programming methodology disclosed in the Wyborny et al. patent is identified herein for illustrative purposes only and that any programming methodology may be employed so long as the desired information is transmitted to and from the pacemaker 11. One of skill in the art may choose from any of a number of available programming techniques to accomplish this task.

Pacemaker 11, illustratively shown in FIG. 2A, is electrically coupled to the patient's heart 16 by lead 14. Lead 14, which includes two conductors, is coupled to a node 52 in the circuitry of pacemaker 11 through input capacitor 50. In the presently disclosed embodiment, an activity sensor 62 provides a sensor output to a processing/amplifying activity circuit 36 of input/output circuit 32. Input/output circuit 32 also contains circuits for interfacing with heart 16, antenna 56, and circuits 44 for application of stimulating pulses to heart 16 to moderate its rate under control of software-implemented algorithms in microcomputer unit 18.

Microcomputer unit 18 comprises on-board circuit 25 which includes microprocessor 20, system clock 22, and on-board RAM 24 and ROM 26. In this illustrative embodiment, off-board circuit 28 comprises a RAM/ROM unit. On-board circuit 25 and off-board circuit 28 are each coupled by a data communication bus 30 to digital controller/timer circuit 34.

The electrical components shown in FIG. 2,4 are powered by an appropriate implantable battery power source 64 in accordance with common practice in the art. For purposes of clarity, the coupling of battery power to the various components of pacemaker 11 is not shown in the figures.

Antenna 56 is connected to input/output circuit 32 to permit uplink/downlink telemetry through RF transmitter and receiver unit 54. Unit 54 may correspond to the telemetry and program logic. disclosed in U.S. Pat. No. 4,556,063 issued to Thompson et al., hereby incorporated by reference herein in its entirety, or to that disclosed in the above-referenced Wyborny et al. patent.

Voltage reference ($V_{REF}$) and bias circuit 60 generates a stable voltage reference and bias current for the analog circuits of input/output circuit 32. Analog-to-digital converter (ADC) and multiplexer unit 58 digitizes analog signals and voltages to provide "real-time" telemetry intracardiac signals and battery end-of-life (EOL) replacement functions.

Operating commands for controlling the timing of pacemaker 11 are coupled by data bus 30 to digital controller/timer circuit 34, where digital timers and counters establish the overall escape interval of the pacemaker as well as various refractory, blanking, and other timing windows for controlling the operation of the peripheral components disposed within input/output circuit 32. Digital controller/timer circuit 34 is preferably coupled to sensing circuitry 38, including sense amplifier 42, peak sense and threshold measurement unit 41, and comparator/threshold detector 40. Sense amplifier 42 amplifies sensed electrocardiac signals and provides an amplified signal to peak sense and threshold measurement circuitry 41. Circuitry 41, in turn, provides an indication of peak sensed voltages and measured sense amplifier threshold voltages on path 43 to digital controller/timer circuit 34. An amplified sense amplifier signal is then provided to comparator/threshold detector 40. Sense amplifier 42 may correspond to that disclosed in U.S. Pat. No. 4,379,459 to Stein, which is hereby incorporated by reference herein in its entirety.

Circuit 34 is further preferably coupled to electrogram (EGM) amplifier 46 for receiving amplified and processed signals sensed by an electrode disposed on lead 14. The electrogram signal provided by EGM amplifier 46 is employed when the implanted device is being interrogated by an external programmer (not shown) to transmit by uplink telemetry a representation of an analog electrogram of the patient's electrical heart activity. Such functionality is, for example, shown in previously referenced U.S. Pat. No. 4,556,063.

Output pulse generator 44 provides pacing stimuli to the patient's heart 16 through coupling capacitor 48 in response to a pacing trigger signal provided by digital controller/timer circuit 34. For example, each time the escape interval times out, an externally transmitted pacing command is received, or such commands are received in response to other stored commands as is well known in pacing art. Output amplifier 44, for example, may correspond generally to the output amplifier disclosed in U.S. Pat. No. 4,476,868 to Thompson, also incorporated by reference herein in its entirety.

Figure 2B:
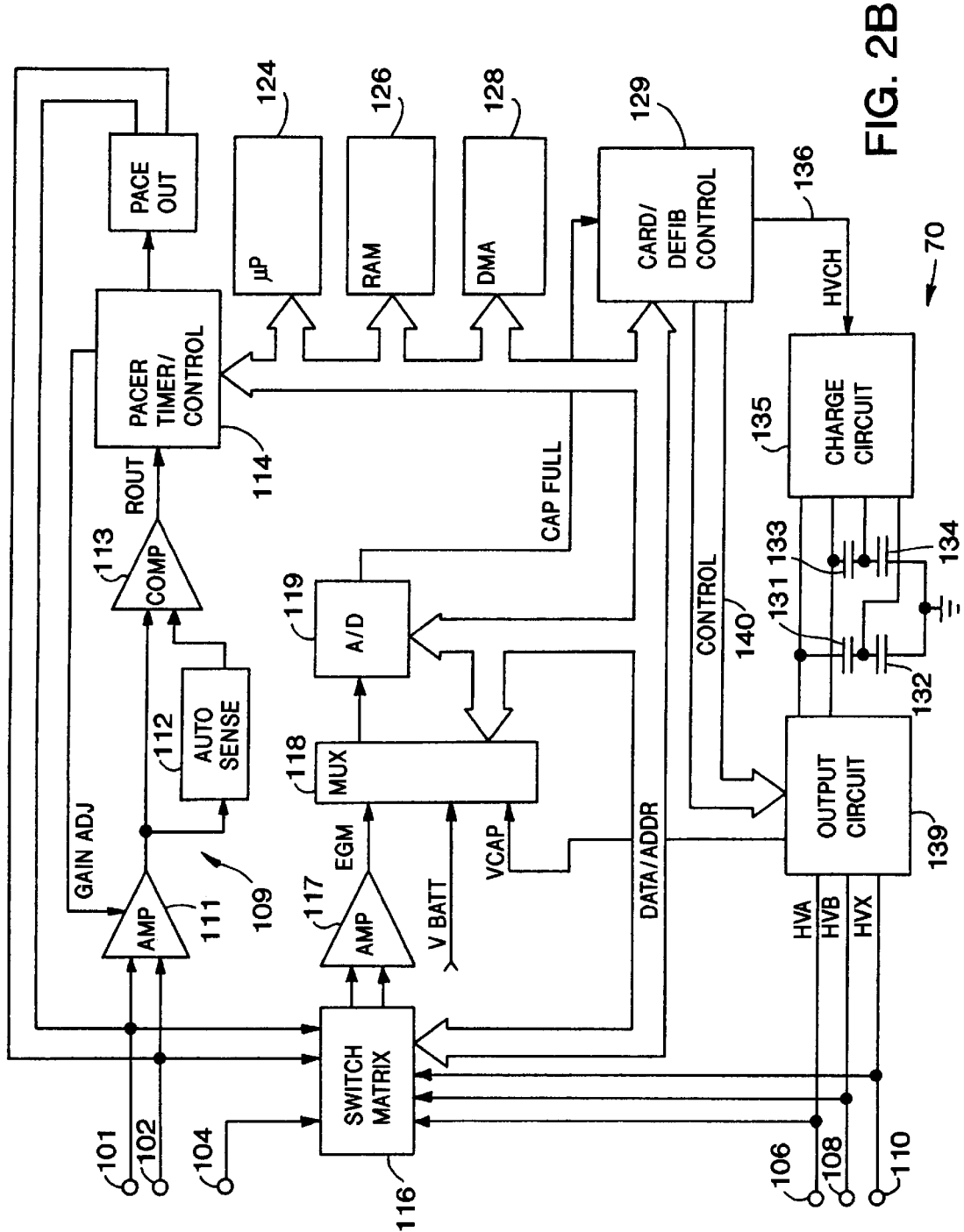
FIG. 2B shows one illustrative embodiment of a pacemaker/cardioverter/defibrillator unit coupled to a dual transducer assembly in accordance with another embodiment of the present invention.

FIG. 2B is a functional schematic diagram from U.S. Pat. No. 5,447,519 to Peterson which shows an implantable pacemaker/cardioverter/defibrillator (PCD) 70 which represents another one of many implantable medical devices that may derive physiologic information from a dual transducer assembly of the present invention. U.S. Pat. No. 5,447,519 is incorporated by reference herein in its entirety. It is understood that this diagram is an illustration of an exemplary type of device in which the invention may find application, and is not intended to limit the scope of the present invention. Other implantable medical devices, such as those described previously, having functional organizations wherein the present invention may be useful, may also be modified to incorporate a dual transducer assembly in accordance with the present invention. For example, the present invention is also believed to be useful in conjunction with implantable pacemakers/cardioverters/defibrillators as disclosed in U.S. Pat. No. 4,548,209 to Wielders, et al.; U.S. Pat. No. 4,693,253 to Adams et al.; U.S. Pat. No. 4,830,006 to Haluska et al.; and U.S. Pat. No. 4,949,730 to Pless et al.; all of which are incorporated herein by reference in their respective entireties.

The PCD device 70 is provided with six electrodes 101, 102, 104, 106, 108, and 110. For example, electrodes 101 and 102 may be a pair of closely-spaced electrodes located in the ventricle. Electrode 104 may correspond to a remote, indifferent electrode located on the housing of the implantable PCD 70. Electrodes 106, 108, and 110 may correspond to large surface area defibrillation electrodes located on device leads or to epicardial electrodes.

Electrodes 101 and 102 are connected to detector circuit 109 which includes band pass filtered amplifier 111, auto-threshold circuit 112, which provides an adjustable sensing threshold, and comparator 113. A signal is generated by the comparator 113 whenever the signal sensed between electrodes 101 and 102 exceeds the sensing threshold defined by auto-threshold circuit 112. Further, the gain of amplifier 111 is adjusted by pacer timing and control circuitry 114. The sense signal, for example, is used to set the timing windows and to align successive waveshape data for morphology detection purposes. For example, the sense event signal may be routed through the pacer/timer control circuit 114 on data bus 115 to processor 124 and may act as an interrupt for processor 124 such that a particular routine of operations is commenced by processor 124.

Switch matrix 116 is used to select available electrodes under the control of processor 124 via data/address bus 115, such that the selection includes two electrodes employed as a far field electrode pair in conjunction with a tachycardia/fibrillation discrimination function. Far field EGM signals from the selected electrodes are passed through band pass amplifier 117 and into multiplexer 118, where they are converted to multi-bit digital data signals by A/D converter 119 for storage in random access memory 126 under the control of direct memory address circuitry 128.

The processor 124 may perform various morphology detection functions. For example, such detection functions may be indicative of tachycardia or fibrillation, or various other functions may be performed as set out in numerous references including any of the references incorporated herein by reference and to others with regard to implantable PCDs.

The remainder of the device 70 of FIG. 213 is dedicated to the provision of cardiac pacing, cardioversion, and defibrillation therapies. The pacer timing/control circuit 114 includes programmable digital counters that control the basic timing intervals associated with cardiac pacing. Further, under control of processor 124, pacer timing/control circuit 114 also determines the amplitude of such cardiac pacing pulses.

In the event that a tachyarrhythmia is detested, and an anti-tachyarrhythmia pacing therapy is desired, appropriate timing intervals for controlling generation of pacing therapies are loaded from processor 124 into pacer timing and control circuitry 114. Similarly, in the event that generation of a cardioversion or defibrillation pulse is required, processor 124 employs the timing and control circuitry 114 to control timing of such cardioversion and defibrillation pulses.

In response to detection of fibrillation or a tachycardia requiring a cardioversion pulse, processor 124 activates cardioversion/defibrillation control circuitry 129, which initiates charging of the high voltage capacitors 131–134 via charging circuit 135 under the control of high voltage charging line 136. Thereafter, delivery and timing of the defibrillation or cardioversion pulse is controlled by pacer timing/control circuitry 114. One embodiment of an appropriate system for delivering and synchronizing cardioversion and defibrillation pulses, and controlling the timing functions related thereto, is disclosed in greater detail in U.S. Pat. No. 5,188,105 to Keimel, which is incorporated herein by reference in its entirety. Other circuitry for controlling the timing and generation of cardioversion and defibrillation pulses is disclosed in U.S. Pat. No. 4,384,585 to Zipes, U.S. Pat. No. 4,949,719 to Pless et al., and in U.S. Pat. No. 4,374,817 to Engle et al., all of which are incorporated herein by reference in their respective entireties. Further, known circuitry for controlling the timing and generation of anti-tachycardia pacing pulses is described in U.S. Pat. No. 4,577,633 to Berkovitz et al., U.S. Pat. No. 4,880,005 to Pless et al., U.S. Pat. No. 4,726,380 to Vollmann et al., and U.S. Pat. No. 4,587,970 to Holley et al., all of which are incorporated herein by reference in their respective entireties.

Selection of a particular electrode configuration for delivery of the cardioversion or defibrillation pulses is controlled via output circuit 139 under the control of cardioversion/defibrillation control circuit 129 via control bus 140. Output circuit 139 determines which of the high voltage electrodes 106, 108 and 110 is to be employed in delivering the defibrillation or cardioversion pulse regimen.

FIG. 3 is a block diagram of an implantable, programmable monitor and lead system which represents another implantable medical device that may derive physiologic information from a dual transducer assembly according to the present invention. The monitor 200 may be embodied as a standalone system or may be embodied as part of pacemaker, PCD, nerve stimulator, or other implantable medical device. FIG. 3 illustrates a patient's heart 16 in relation to a lead 14 to which a dual transducer assembly 1,7 in accordance with one embodiment of the present invention is coupled The lead 14 includes first and second lead conductors 13 and 15 extending from a proximal connector end 18 to the dual transducer assembly 17 disposed near the distal tine assembly 27. The tine assembly 27 includes soft pliant tines adapted to catch in heart tissue to stabilize the lead in a manner well known in pacing art.

Monitor 200 is divided generally into an input/output circuit 212 coupled to a battery 208, an optional activity sensor 206, a telemetry antenna 234, the lead conductors 13, 15, a crystal 210, and a microcomputer circuit 214. The input/output circuit 212 includes the digital controller/timer circuit 232 and the associated components including the crystal oscillator 238, power-on-reset (POR) circuit 248, Vref/BIAS circuit 240, ADC/MUX circuit 242, RF transmitter/receiver circuit 236, optional activity circuit 252, and sensor signal demodulator 250.

Crystal oscillator circuit 238 and crystal 210 provide the basic timing clock signals for the digital controller/timer circuit 232. Voltage Reference ($V_{ref}$)/BIAS circuit 240 generates stable voltage reference Vref and current levels from battery 208 for the circuits within the digital controller/timer circuit 232, and the other identified circuits including microcomputer circuit 214 and demodulator 250. Power-on-reset circuit 248 responds to initial connection of the circuitry to the battery 208 for defining an initial operating condition and also resets the operating condition in response to detection of a low battery voltage condition. Analog-to-digital converter (ADC) and multiplexer circuit 142 digitizes analog sensor signals received by digital controller/timer circuit 232 from demodulator 250 for storage by microcomputer circuit 214.

Data signals transmitted out through RF transmitter/receiver circuit 236 during telemetry are multiplexed by ADC/MUX circuit 242. Voltage reference and bias circuit 240, ADC/MUX circuit 242, POR circuit 248, crystal oscillator circuit 238, and optional activity circuit 252 may correspond to any of those previously described herein or presently used in current marketed, implantable cardiac pacemakers.

Digital controller/timer circuit 232 includes a set of timers and associated logic circuits connected with the microcomputer circuit 214 through the data communications bus 230. Microcomputer circuit 214 contains an on-board chip including microprocessor 220, associated system clock 222, and on-board RAM and ROM chips 224 and 226, respectively. In addition, microcomputer circuit 214 includes an off-board circuit 218 including separate RAM/ROM chip 228 to provide additional memory capacity. Microprocessor 220 is interrupt driven, operating in a reduced power consumption mode normally, and awakened in response to defined interrupt events, which may include the periodic timing out of data sampling intervals for storage of monitored data, the transfer of triggering and data signals on the bus 230, and the receipt of programming signals. A real time clock and calendar function may also be included to correlate stored data to time and date.

In a further variation, provision may be made for the patient to initiate storage of the monitored data through an external programmer or a reed switch closure when an unusual event or symptom is experienced. The monitored data may be related to an event marker on later telemetry out and examination by the physician.

Microcomputer circuit 214 controls the operating functions of digital controller/timer 232, specifying which timing intervals are employed, and controlling the duration of the various timing intervals, via the bus 230. The specific current operating modes and interval values are programmable. The programmed-in parameter values and operating modes are received through the antenna 234, demodulated in the RF transmitter/receiver circuit 236, and stored in RAM 224.

Data transmission to and from the external programmer (not shown) is accomplished by means of the telemetry antenna 234 and the associated RF transmitter and receiver 236, which serves both to demodulate received downlink telemetry and to transmit uplink telemetry. For example, circuitry for demodulating and decoding downlink telemetry may correspond to that disclosed in previously referenced U.S. Pat. No. 4,556,063 and U.S. Pat. No. 4,257,423 issued to McDonald et al., while uplink telemetry functions may be provided according to U.S. Pat. No. 5,127,404 issued to Wyborny et al., each of which is hereby incorporated by reference herein in their respective entireties. Uplink to telemetry capabilities typically include the ability to transmit stored digital information as well as real time physiologic sensor signals, such as blood pressure signals for example.

A number of power, timing, and control signals are applied by the digital controller/timer circuit 232 to the demodulator 250 to selectively initiate and power the operation of each of the two independent physiologic sensors 19, 20 included within the dual transducer assembly 17, and to selectively read out the applicable signals generated by the dual transducer assembly sensors 19, 20. The monitor 200 periodically stores digitized data related to the various physiologic parameters sensed by the dual transducer assembly 17 at a nominal sampling frequency which may be related to patient activity level, both optionally correlated to time and date and patient initiated event markers. Depending on the particular configuration of the dual transducer assembly 17, pertinent physiologic parameters, such as parameters relating to patient activity, blood pressure and/or temperature, blood oxygen or other gas saturation level, and electrogram (EGM) status, may be continuously monitored.

Figure 4:
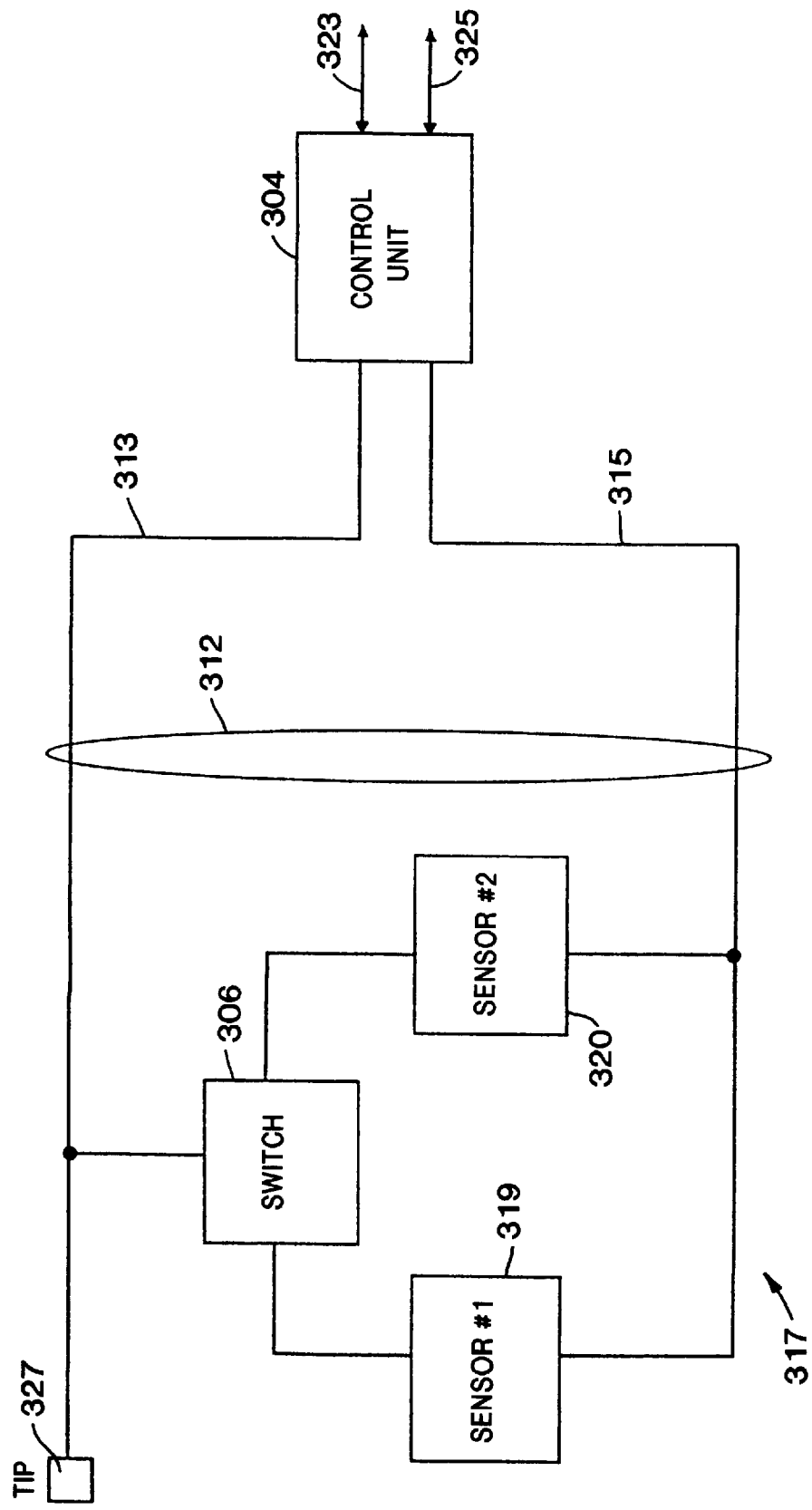
FIG. 4 shows a switching architecture for selectively activating and deactivating each of two sensors coupled to a pair of lead conductors in accordance with one embodiment of the present invention.

FIG. 4 is a block diagram useful for describing various structural and functional features of one embodiment of a dual transducer assembly according to the present invention. In accordance with this illustrative embodiment, the dual transducer assembly 317 includes two sensors sensor #1 319 and sensor #2 320, each of which senses one or more physiologic parameters associated with a human heart or other organ. Sensors #1 319 and #2 320 represent two sensors which may be fabricated as discrete or, alternatively, integral IC components. A switch 306 is coupled to sensors #1 319 and #2 320 and to one conductor 313 of the two conductor lead 312. Sensors #1 319 and #2 320 are also coupled to a second conductor 315 of the lead 312. The construction and configuration of conductors 313, 315 and attachments are of a conventional type as is known in the art of pacing lead technology.

Conductors 313, 315 are coupled to a control unit 304. Control unit 304 is intended to represent a component or set of components that perform the general functions of controlling the state of the two conductors 313, 315 and coordinating the transmission and reception of signals over the conductor pair 313, 315. Control unit 304, for example, may represent a controller circuit, such as digital controller/timer circuit 232 shown in FIG. 3, or a control circuit incorporating the functionality of a decoder circuit, such as demodulator 250 also shown in FIG. 3. Control unit 304 may further be representative of a microprocessor, such as microcomputer circuit 214 shown in FIG. 3, alone or in combination with other components shown in FIG. 3. Various signals transmitted between the sensors #1 319 and #2 320 and the control unit 304 may be processed or produced by other such components via signal conductors 323, 325.

As is further shown in FIG. 4, a tine electrode, TIP 327, is tropically connected to appropriate heart or other organ tissue as discussed previously. Electrical signals attendant to the depolarizatior and re-polarization of the heart are transmitted from TIP electrode 327 to control unit 304. In a typical manner of operation, the control unit 304, in response to electrical signals received from the TIP electrode 327, applies a supply voltage, $V_{SUPP}$, across the pair of conductors 313, 315 of a pre-established polarity so as to selectively and alternately activate and deactivate sensors #1 319 and #2 320 via switch 306. Switch 306 senses the presence and polarity of the supply voltage, $V_{SUPP}$.

In response to a supply voltage, $V_{SUPP}$, of a positive polarity applied to conductors 313, 315 by control unit 304, for example, switch 306 delivers the supply voltage, $V_{SUPP}$, to sensor #1 319 to activate sensor #1 319 for operation. Switch 306, when activating sensor #1 319, concurrently removes the supply voltage, $V_{SUPP}$, from sensor #2 320. In response to a supply voltage, $V_{SUPP}$, of a positive polarity produced by control unit 304 and applied to conductors 313, 315, switch 306 delivers the supply voltage, $V_{SUPP}$, to sensor #2 320 to activate sensor #2 320 for operation, and concurrently removes the supply voltage, $V_{SUPP}$, from sensor #1 319. In this embodiment, switch 306 is employed to select and deselect sensors #1 319 and #2 320 for operation by providing power only to a selected one of the two sensors #1 319 and #2 320.

This power switching methodology advantageously reduces the amount of power consumed by sensors #1 319 and #2 320 over time, and reduces the overall power requirements of the medical device coupled to the dual transducer assembly 317. It is noted that various components of the control unit 304, such as the demodulator 250 shown in FIG. 3 according to one embodiment of the present invention, may also be activated and deactivated during periods in which neither one of the two sensors #1 319 and #2 320 are active.

Each of the sensors #1 319 and #2 320, when selected for operation by the switch 306, has exclusive use of the pair of conductors 313, 315 for communicating its respective physiologic data to control unit 304. The need to arbitrate between disparate sensor signals each competing for access to the conductor pair 312 is thus obviated using a power switching methodology in accordance with the principles of the present invention. Increased reliability and data integrity may be realized by employment of this simple yet elegant switching architecture.

Figure 5:
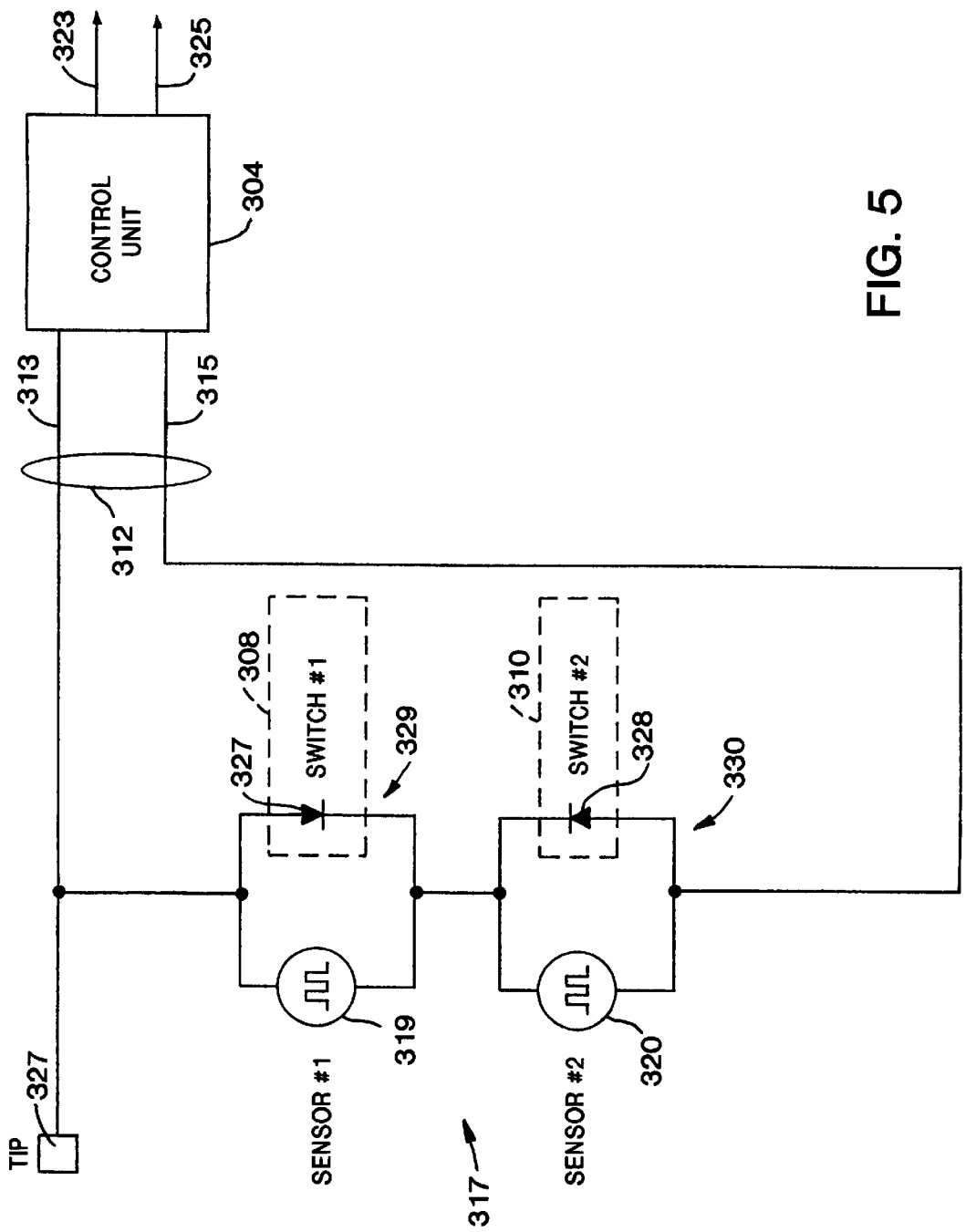
FIG. 5 shows a switching architecture for selectively activating and deactivating each of two sensors connected in series to a pair of lead conductors in accordance with another embodiment of the present invention.

FIG. 5 is a block diagram of a dual transducer assembly configured in a series arrangement with respect to the conductor pair 312 in accordance with one embodiment of the present invention. In this illustrative embodiment, sensor #1 319 is connected in parallel with switch #1 308, which includes diode 327, to define sensor unit #1 329. Sensor #2 320 is connected in parallel with switch #2 310, which includes diode 328, to define sensor unit #2 330. The polarity of diode 327 in sensor unit #1 329 is opposite to that of diode 328 in sensor unit #2 330. Sensor unit #1 329 is connected in series with sensor unit #2 330 and to conductors 313 and 315. In one embodiment, diodes 327, 328 are parasitic substrate diodes. In another embodiment, diodes 327, 328 are discrete components.

In this configuration, control unit 304 activates sensor #2 320 by applying a supply voltage, $V_{SUPP}$, having a positive polarity across conductors 313, 315. A supply voltage, $V_{SUPP}$, of a positive polarity reverse biases diode 328 of switch #2 310 and causes diode 327 of switch #1 308 to conduct. Diode 327 of switch #1 308, when conducting, acts as a shunt across sensor #1 319, resulting in deactivation of sensor #1 319 and activation of sensor #2 320. In this manner, no power is consumed by sensor #1 319 during operation of sensor #2 320.

Control unit 304 deactivates sensor #2 320 and activates sensor #1 319 by applying a supply voltage, $V_{SUPP}$, having a negative polarity across conductors 313, 315. A negative supply voltage, $V_{SUPP}$, reverse biases diode 327 of switch #1 308 and causes diode 328 of switch #2 310 to conduct. While in a forward biased mode, diode 328 of switch #2 310 acts as a shunt across sensor #2 320, resulting in deactivation of sensor #2 320 and activation of sensor #1 319. It can be seen that no power is consumed by sensor #2 320 during operation of sensor #1 319.

Figure 6:
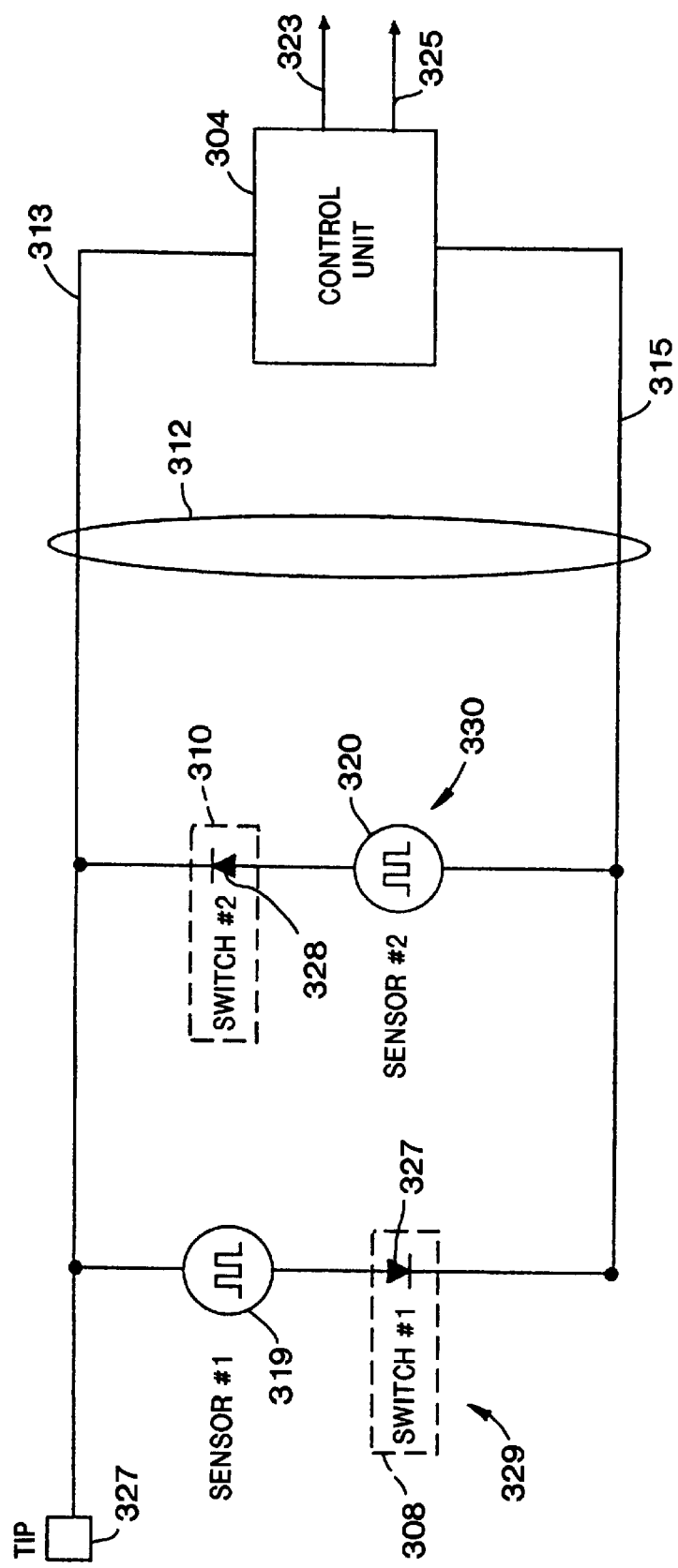
FIG. 6 shows a switching architecture for selectively activating and deactivating each of two sensors connected in parallel to a pair of lead conductors in accordance with a further embodiment of the present invention.

FIG. 6 is a block diagram of an alternative dual transducer assembly configuration in accordance with another embodiment of the present invention. In this configuration, sensor #1 319 is connected in series with diode 327 of switch #1 308 to define sensor unit #1 329. Sensor #2 320 is connected in series with diode 328 of switch #2 310 to define sensor unit #1 330. Sensor units #1 329 and #2 330 are connected in parallel to conductors 313 and 315.

Sensor #2 320 is activated by control unit 304 by application of a positive supply voltage, $V_{SUPP}$, to conductors 313, 315. The positive supply voltage, $V_{SUPP}$, forward biases diode 327 of switch #1 308 and reverse biases diode 328 of switch #2 310. In a manner described previously with regard to the embodiment of FIG. 4, forward biased diode 327 of switch #1 308 acts as a shunt across sensor #1 319, resulting in deactivation of sensor #1 319. Reverse biased diode 328 of switch 310 provides for activation of sensor #2 320.

Control unit 304 deactivates sensor #2 320 and activates sensor #1 319 by applying a negative supply voltage, $V_{SUPP}$, to conductors 313, 315. The negative supply voltage, $V_{SUPP}$, causes diode 328 of switch #2 310 to conduct and reverse biases diode 327 of switch #1 308. Diode 328 of switch #2 310 acts as a shunt across sensor #2 320, resulting in deactivation of sensor #2 320 and activation of sensor #1 319. It can be seen from FIGS. 4 and 5 that the dual transducer assembly of the present invention may be employed in both series and parallel configurations.

Figure 7:
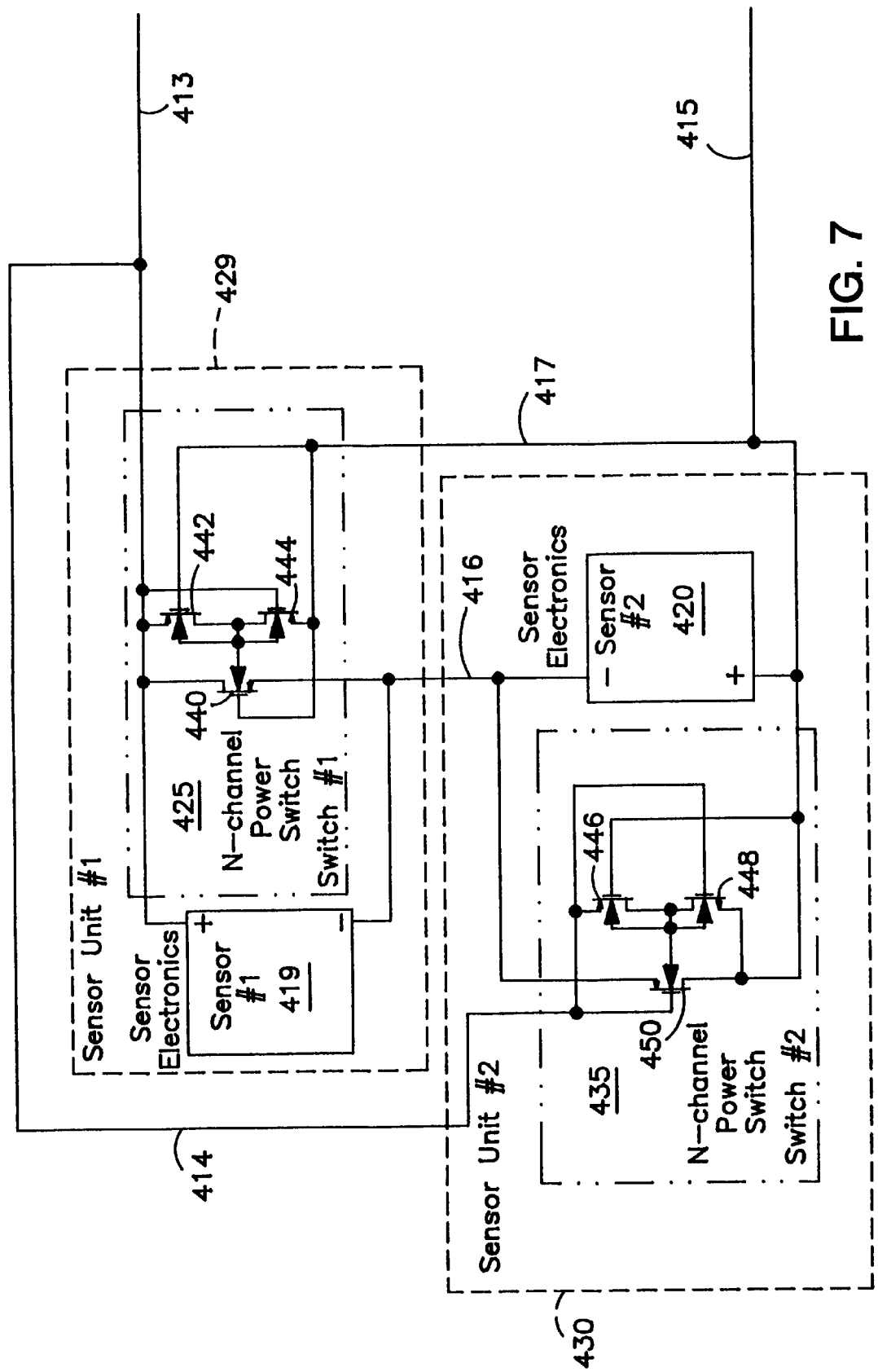
FIG. 7 shows a schematic drawing of a switching circuit employing n-channel transistors for selectively activating and deactivating each of two sensors connected in series to a pair of lead conductors in accordance with one embodiment of the present invention.
Figure 8B:
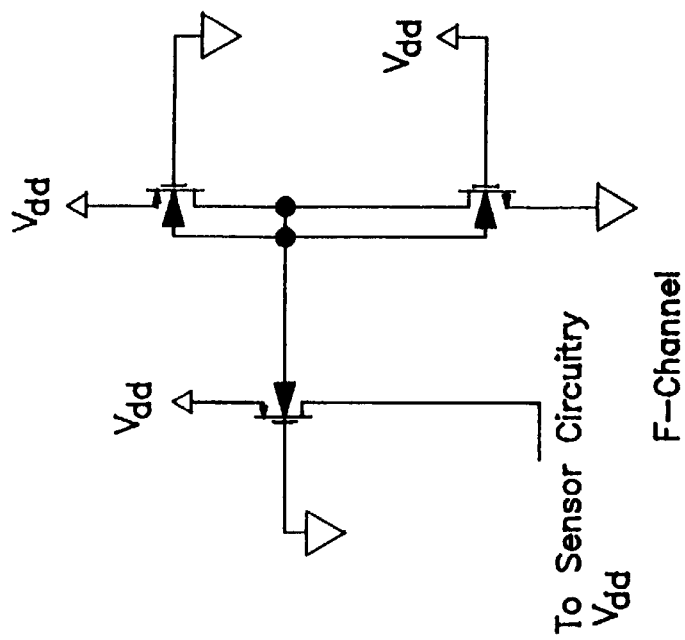
FIG. 8B shows a schematic drawing of power switch employing one or more p-channel transistors in accordance with another embodiment of the present invention.
Figure 8A:
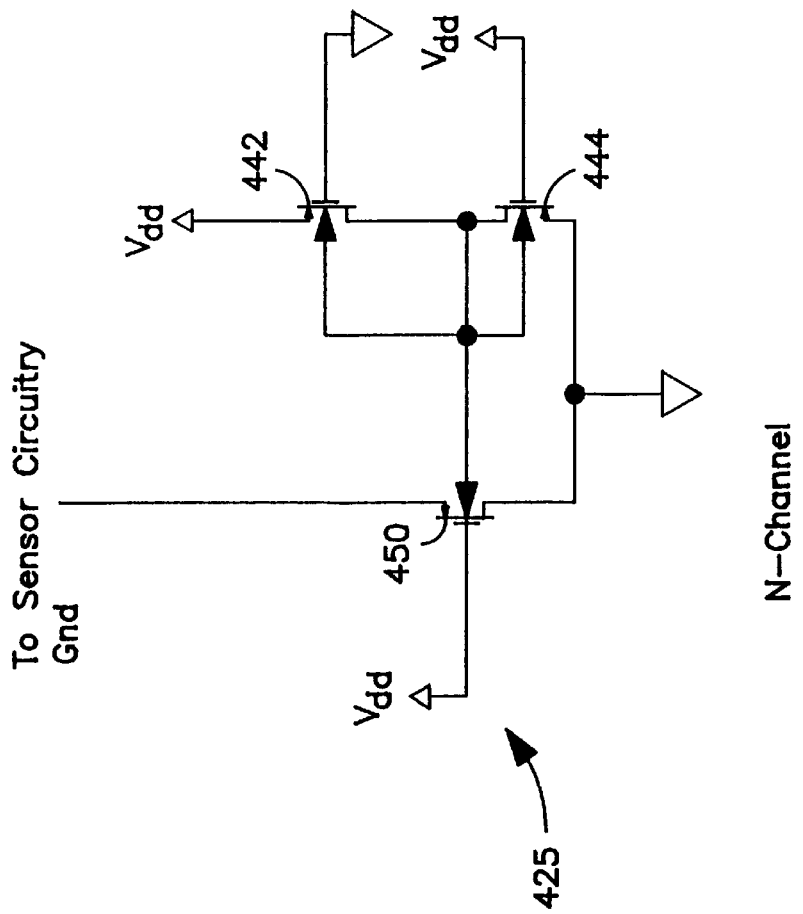
FIG. 8A shows a schematic drawing of power switch employing one or more n-channel transistors in accordance with an embodiment of the present invention.

FIG. 7 is a schematic diagram of a dual transducer assembly in accordance with an alternative embodiment of the present invention. In this embodiment, n-channel MOSFET transistors are employed in each of the switches #1 425 and #2 435, which are connected in parallel with corresponding sensors #1 419 and #2 420, respectively. An enlarged schematic diagram of switch #1 425 is shown in FIG. 8A. Sensor unit #1 429, which includes sensor #1 419 and switch #1 425, is connected in series with sensor unit #2 430, which includes sensor #2 420 and switch #2 435.

Switch #1 425 controls activation and deactivation of sensor #1 419 through n-channel power transistor 440 and n-channel switching transistors 442 and 444. Switch #2 435 controls activation and deactivation of sensor #2 420 through n-channel power transistor 450 and n-channel switching transistors 446 and 448. Lead conductor 413 is coupled to the positive power contact of sensor #1 419 and switch #1 425. Lead conductor 415 is coupled to the positive power contact of sensor #2 420 and switch #2 435. Conductor 414 connects lead conductor 413 to the gate of n-channel power transistor 450 of switch #2 435.

Conductor 416 is connected to the negative power contact of sensor #1 419, and is coupled to lead conductor 413 via the source of n-channel power transistor 440 of switch #1 425. Conductor 416 is also connected to the negative power contact of sensor #2 420, and is coupled to lead conductor 415 via the source of n-channel power transistor 450 of switch #2 435. Conductor 417 connects conductor lead 415 with the source of switching transistor 444 and the gates of power transistor 440 and switching transistor 442, respectively. Other interconnections of interest between the various components are shown in the schematic diagram of FIG. 7.

It can be seen from FIG. 7 that varying the polarity of a supply voltage, $V_{SUPP}$, applied across lead conductors 413 and 415 selectively activates and deactivates power transistors 440 and 450 of switches #1 419 and #2 420 which, in turn, deactivates and activates sensors #1 413 and #2 420, respectively. It is noted that p-channel power transistors may be used in place of n-channel power transistors 440 and 450, assuming that the appropriate reversal of sensor power contact polarities is made. It is further noted that other types of transistors, such as bipolar transistors, JFETs, MESFETS, or DFETs for example, may be use in the construction of switches #1 425 and #2 435 in this and other embodiments described herein, the implementations of which may readily be accomplished by one skilled in the art. Further, substrate, discrete, or hybrid transistor implementations may be employed as is appropriate for a given application.

Figure 9:
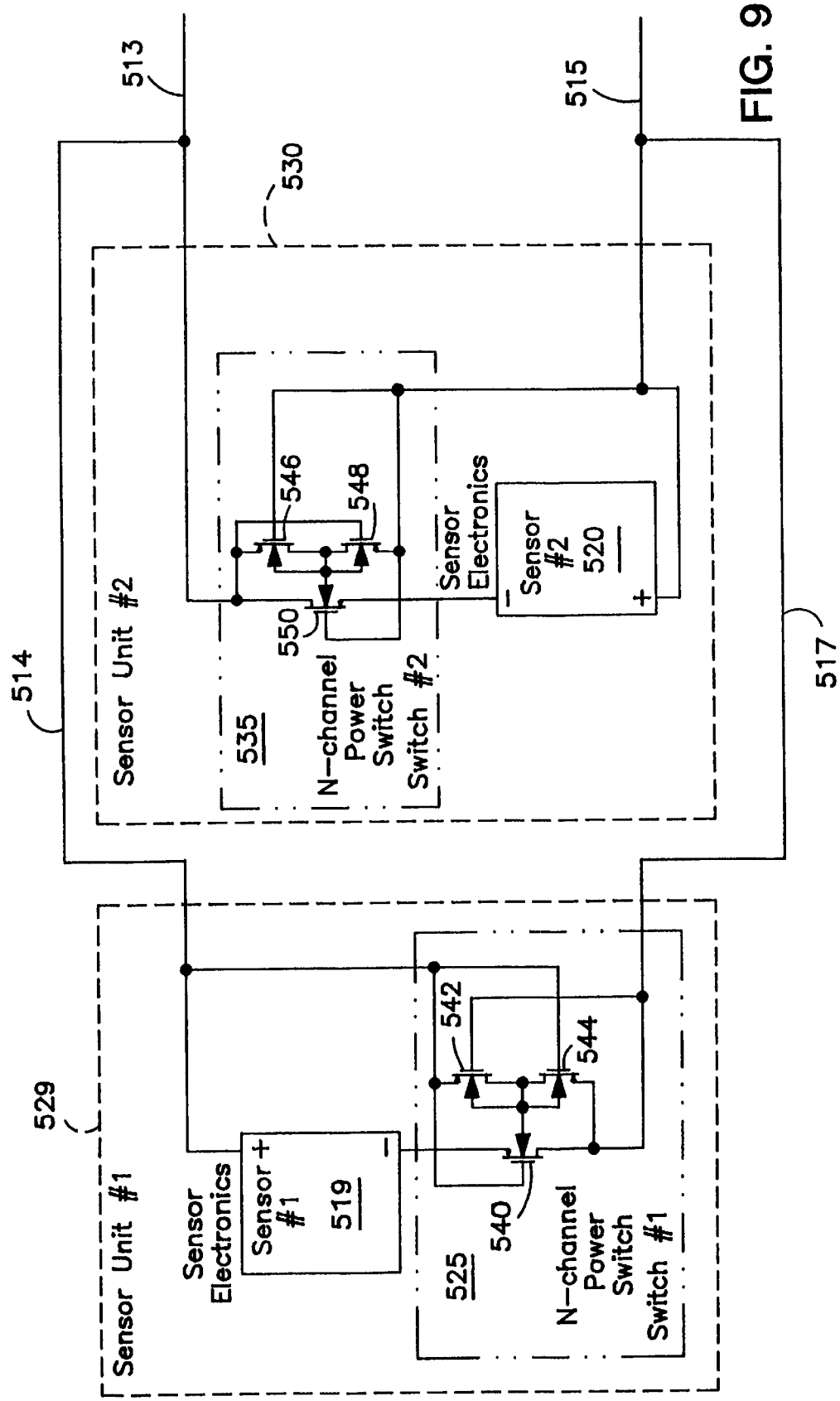
FIG. 9 shows a schematic drawing of a switching circuit employing n-channel transistors for selectively activating and deactivating each of two sensors connected in parallel to a pair of lead conductors in accordance with one embodiment of the present invention.

FIG. 9 is a schematic diagram of a dual transducer assembly in accordance with another embodiment of the present invention. In this embodiment, n-channel MOSFET transistors are employed in each of the switches #1 525 and #2 535, which are connected in series with sensors #1 519 and #2 520, respectively. Sensor unit #1 529, which includes sensor #1 519 and switch #1 525, is connected in parallel with sensor unit #2 530, which includes sensor #2 520 and switch #2 535.

Switch #1 525 controls activation and deactivation of sensor #1 519 through n-channel power transistor 540 and n-channel switching transistors 542 and 544. Switch #2 535 controls activation and deactivation of sensor #2 520 through n-channel power transistor 550 and n-channel switching transistors 546 and 548. The interconnections between the various component are readily perceivable to one skilled in the art by referencing the schematic drawing shown in FIG. 9.

From FIG. 9, it can be seen that varying the polarity of a supply voltage, $V_{SUPP}$, applied across lead conductors 513 and 515 selectively activates and deactivates power transistors 540 and 550 of switches #1 519 and #2 520 which, in turn, deactivates and activates sensors #1 519 and #2 520, respectively. As with the series embodiment shown in FIG. 7, p-channel power transistors may be used in place of the n-channel power transistors 540 and 550, assuming that the appropriate reversal of sensor power contact polarities is made.

Figure 10:
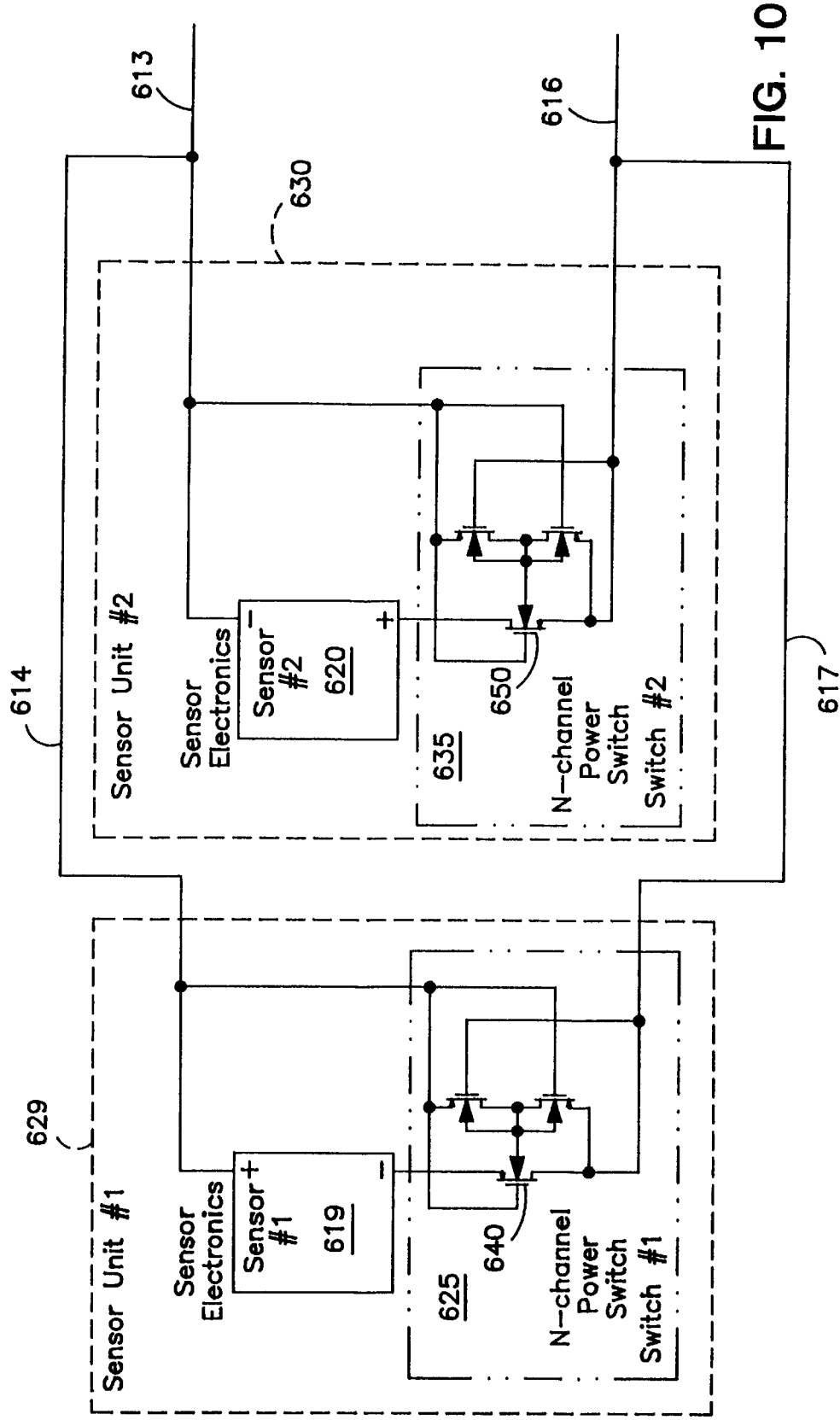
FIG. 10 shows a schematic drawing of a switching circuit employing n-channel and p-channel transistors for selectively activating and deactivating each of two sensors connected in parallel to a pair of lead conductors in accordance with another embodiment of the present invention.

FIG. 10 is a schematic drawings of yet another embodiment of a dual transducer assembly according to the present invention. The dual transducer shown in FIG. 10 includes sensors #1 619 and #2 620 connected in parallel to lead conductors 613 and 615. In this embodiment, switch #1 615 includes n-channel MOSFET transistors and switch #2 635 includes p-channel MOSFET transistors. The switching functionality of the dual transducer assembly shown in FIG. 10 is similar to that described previously with regard to the embodiments shown in FIGS. 7 and 9. An enlarged schematic diagram of p-channel power switch #2 650 is shown in FIG. 8B. As with the previously described embodiments, varying the polarity of a supply voltage, $V_{SUPP}$, applied across lead conductors 613 and 615 selectively activates and deactivates power transistors 640 and 650 of switches #1 619 and #2 620 which in turn, deactivates and activates sensors #1 619 and #2 620, respectively A number of factors should be considered when designing or selecting the n-channel or p-channel power MOSFET transistors, such as transistors 640 and 650 shown in FIG. 10, respectively. These factors include current draw of the sensor circuitry, the acceptable voltage drop from the power transistor to the sensor, and the bias voltage of the sensor. In general, the desirable characteristics of a power MOSFET well suited for use in a dual transducer assembly according to one or more embodiments of the present invention include a wider and shorter channel length for higher current consumption, a lower acceptable voltage drop, and a lower sensor bias voltage. These general characteristics are also desirable when designing or selecting switching MOSFETs that may be incorporated into the sensor control circuitry employed in the control unit 304 or other controlling medical device.

Figure 11:
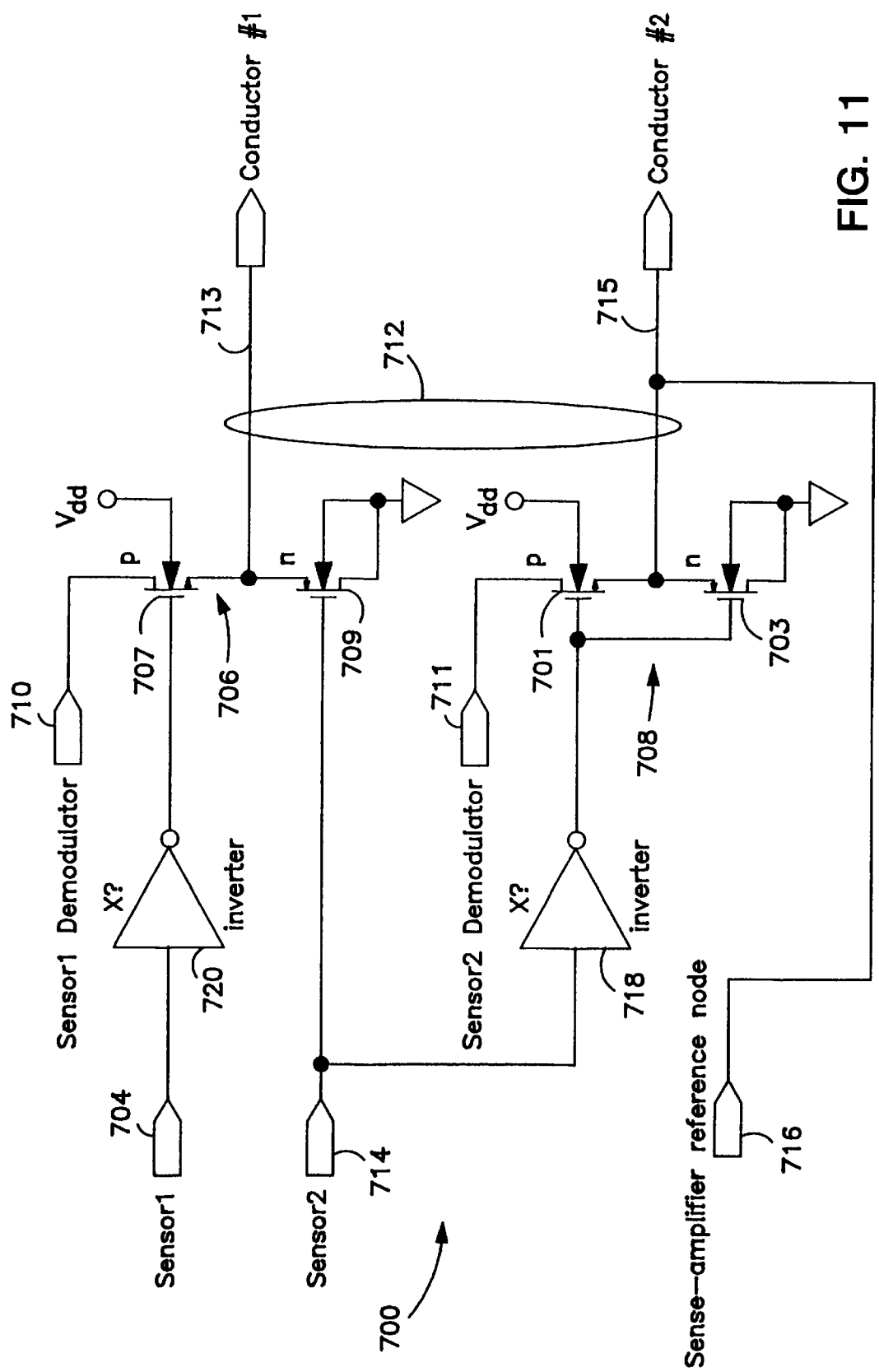
FIG. 11 shows a schematic drawing of interface circuitry for interfacing a dual transducer assembly with a control unit or recovery unit of an implantable medical device in accordance with one embodiment of the present invention.

FIG. 11 is a schematic diagram of interlace circuitry 700 which may be useful when interfacing a dual transducer assembly according to the present invention with a control unit or recovery unit, such as the applicable components of pacemaker 11 or monitor 200 shown in FIGS. 2 and 3, respectively. The interface circuitry 700 is typically incorporated as part of the input/output circuitry of the control or recovery unit.

In this embodiment, conductor #2 715 of the two conductor lead 712 is coupled to a TIP conductor (not shown) implanted in a human heart, for example. The TIP conductor senses electrical activation of the myocardial tissue of the heart. The sensor #2 input/output contact 716 is typically coupled to an electrogram (EGM) amplifier, such as EGM amplifier 46 shown in FIG. 2A. The sense amplifier reference contact 716 is typically coupled to a sense amplifier, such as sense amplifier 42 shown in FIG. 2A. Conductor #1 715 is coupled to an output amplifier, such as output amplifier 44 shown in FIG. 2A. In one embodiment, output amplifier 44 is an output pulse generator that provides pacing stimuli to the heart in response to a pacing trigger signal provided by a digital controller/timer circuit, such as circuit 34 shown in FIG. 2A.

The interface circuitry 700 shown in FIG. 11 further includes driver 706 which is coupled to conductor #1 713 and inverter 720, which in turn is connected to sensor #1 input/output contact 704. In this embodiment, driver 706 is a CMOS switch which includes an NMOS driver transistor 709 and a PMOS load transistor 707. Driver 708 is coupled to conductor #2 715 and both the sense amplifier contact reference contact 716 and the sensor #2 input/output contact 714 through inverter 718. Driver 708 also constitutes a CMOS switch which includes an NMOS driver transistor 703 and a PMOS load transistor 701. It is noted that in pacing applications, conductor #2 715 is used as the pacing conductor. The operation of the interface circuitry 700 in response to various voltage signals developed on conductors #1 713 and #2 715 and to signals applied to contacts 710, 704, 714, and 716 will be readily understood by one skilled in the art.

The sensors discussed hereinabove with reference to FIGS. 4–11 have been generally described in a generic manner, since it is intended that any suitable implantable physiologic sensor may be incorporated as part of a dual transducer assembly according to the present invention. The following list of sensor types is provided to illustrate various known implantable physiologic sensors that are well suited for incorporation into a dual transducer assembly of the present invention. It is to be understood that this non-exhaustive list of sensor types is provided for illustrative purposes only, and is not intended to limit the type of sensor that may be employed in a dual transducer assembly. These sensors include: capacitive absolute pressure sensors; optical based oxygen saturation sensors; piezo-resistive absolute pressure sensors; relative pressure sensors; acceleration or activity sensors; electro-chemical sensors, such as oxygen sensors and glucose sensors; doppler flow sensors; strain gauge sensors; and electronic thermo-dilution sensors.

In one embodiment of the present, the dual transducer assembly 17 shown in FIG. 3 includes a pressure sensor 20 and an oxygen saturation sensor 19. An exemplary capacitive absolute pressure sensor well suited for use in the dual transducer assembly 17 is described in U.S. Pat. Nos. 5,535,752 and 5,564,434, both of which are issued to Halperin et al. and incorporated herein by reference in their respective entireties. It is noted that the capacitive absolute pressure sensor disclosed in U.S. Pat. Nos. 5,535,752 and 5,564,434 represents a single sensor that monitors two distinct physiologic parameters, namely, an absolute blood pressure parameter and a blood temperature parameter.

In addition to a capacitive absolute pressure sensor, the dual transducer assembly 17 in accordance with this illustrative embodiment includes an oxygen saturation sensor 19. An exemplary oxygen saturation sensor well suited for use in the dual transducer assembly 17 is described in U.S. Pat. Nos. 4,750,495 and 4,903,701, both of which are issued to Moore et al. and incorporated herein by reference in their respective entireties.

The preceding specific embodiments are illustrative of the practice of the invention. It is to be understood, therefore, that other expedients known to those killed in the art or disclosed herein may be employed without departing from the invention or the scope of the appended claims. For example, the present invention is not limited to use of a dual transducer assembly in conjunction with a particular implantable medical device, such as a pacemaker, but may be used in conjunction with other medical devices as well. The present invention is also not limited to specific data acquisition and communications techniques, such as those presented herein, but such functions may be directed using other like techniques. The present invention further includes; within its scope methods of using the dual transducer assembly as well as the structural particulars described hereinabove.

In the claims, means plus function clauses are intended to cover the an. structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

What is claimed is:

1. A body implantable dual transducer apparatus comprising:
   a first sensor that senses a first physiologic parameter and provides a first sensor signal when powered by a supply voltage of a first polarity;
   a second sensor that senses a second physiologic parameter and provides a second signal when powered by a supply voltage of a second polarity;
   a pair of conductors coupled to the first and second sensors;
   a control unit that selectively applies the supply voltage of either the first polarity or the second polarity across the pair of conductors; and
   switching circuitry that, in response to the supply voltage of the first polarity, provides the supply voltage of the first polarity to the first sensor for generating the first sensor signal, and in response to the supply voltage of the second polarity, provides the supply voltage of the second polarity to the second sensor for generating the second sensor signal, the first and second sensor signals being transmitted to the control unit using the pair of conductors wherein at least one of the sensors senses a plurality of different physiological parameters.

2. The apparatus of claim 1, wherein the first and second sensors are coupled in parallel with the pair of conductors, and the switching circuitry further comprises:
   a first switch connected in series with the first sensor and a second switch connected in series with the second sensor, the first and second switches, in response to the supply voltage of the first polarity, cooperatively operating to provide the supply voltage of the first polarity to the first sensor and remove any supply voltage from the second sensor, and the first and second switches, in response to the supply voltage of the second polarity, cooperatively operating to provide the supply voltage of the second polarity to the second sensor and remove any supply voltage from the first sensor.

3. The apparatus of claim 2, wherein each of the first and second switches comprises at least one n-channel FET transistor or one npn BJT transistor.

4. The apparatus of claim 2, wherein each of the first and second switches comprises at least one p-channel FET transistor or one to npn BJT transistor.

5. The apparatus of claim 2, wherein the first switch comprises at least one n-channel transistor and the second switch comprises at least one p-channel transistor.

6. The apparatus of claim 2, wherein each of the first and second switches comprises a substrate switch.

7. The apparatus of claim 2, wherein each of the first and second switches comprises a diode.

8. The apparatus of claim 2, wherein each of the first and second switches comprises a substrate diode.

9. The apparatus of claim 1, wherein the first and second sensors are coupled in series to the pair of conductors, and the switching circuitry further comprises:
   a first switch connected in parallel with the first sensor, the first switch is closed in response to the supply voltage of the second polarity, thereby conducting a supply current to the second sensor and removing the supply voltage from the first sensor and providing the supply voltage of the second polarity to the second sensor; and
   a second switch connected in parallel with the second sensor, the second switch is closed in response to the supply voltage of the first polarity, thereby conducting the supply current to the first sensor and removing the supply voltage from the second sensor and providing the supply voltage of the first polarity to the first sensor.

10. The apparatus of claim 9, wherein each of the first and second switches comprises at least one n-channel FET transistor or one npn BJT transistor.

11. The apparatus of claim 9, wherein each of the first and second switches comprises at least one p-channel transistor or one pnp BJT transistor.

12. The apparatus of claim 9, wherein the first switch comprises at least one n-channel transistor and the second switch comprises at least one p-channel transistor.

13. The apparatus of claim 9, wherein each of the first and second switches comprises a substrate switch.

14. The apparatus of claim 9, wherein each of the first and second switches comprises a diode.

15. The apparatus of claim 9, wherein each of the first and second switches comprises a substrate diode.

16. The apparatus of claim 1, wherein the first and second sensors are connected in series to the pair of conductors.

17. The apparatus of claim 1, wherein the first and second sensors are connected in parallel to the pair of conductors.

18. The apparatus of claim 1, wherein the control unit comprises an implantable medical device.

19. A body implantable dual transducer apparatus, the apparatus comprising:
   a control unit that selectively supplies a control signal of a first polarity or a control signal of a second polarity;
   a first sensor that senses a first physiologic parameter;
   a second sensor that senses a second physiologic parameter;
   a pair of conductors coupled to the first and second sensors and to the control unit; and
   switching circuitry coupled to the control unit that selectively activates one of the first or second sensors and deactivates the other one of the first or second sensors in response to control signals of the first and second polarities produced by the control device wherein at least one of the sensors senses a plurality of different physiological parameters.

20. The apparatus of claim 19, wherein the first and second sensors are coupled in series to the pair of conductors, and the switching circuitry comprises:
   a first switch connected in parallel with the first sensor, the first switch activating the second sensor and deactivating the first sensor in response to the control signal of the second polarity; and
   a second switch connected in parallel with the second sensor, the second switch activating the first sensor and deactivating the second sensor in response to the control signal of the first polarity.

21. The apparatus of claim 20, wherein each of the first and second switches is selected from the group consisting of an n-channel FET transistor, a p-channel FET transistor, a diode, an npn BJT transistor or a pnp BJT transistor.

22. The apparatus of claim 21, wherein each of the first and second switches comprises substrate switches.

23. The apparatus of claim 19, wherein the first and second sensors are coupled in parallel to the pair of conductors, and the switching circuitry comprises:

a first switch connected in series with the first sensor and a second switch connected in series with the second sensor, the first and second switches, in response to the control signal of a second polarity, cooperatively operating to activate the second sensor and deactivate the first sensor, and the first and second switches, in response to the control signal of a first polarity, cooperatively operating to activate the first sensor and deactivate the second sensor.

24. The apparatus of claim 23, wherein each of the first and second switches is selected from the group consisting of an n-channel FET transistor, a p-channel FET transistor, a diode, an npn BJT transistor or a pnp BJT transistor.

25. The apparatus of claim 23, wherein each of the first and second switches comprises substrate switches.

26. A method of controlling a body implantable dual transducer apparatus including a first sensor that senses a first physiologic parameter and generates a first sensor signal and a second sensor that senses a second physiologic parameter and generates a second sensor signal, the first and second sensors coupled to an implantable medical device via a pair of conductors, the method comprising:

selectively applying a voltage of either a first polarity or a second polarity across the pair of conductors;

providing, in response to the voltage of the first polarity, power to the first sensor for generating the first sensor signal and concurrently removing power from the second sensor;

providing, in response to the voltage of the second polarity, power to the second sensor for generating the second sensor signal and concurrently removing power from the first sensor; and transmitting the first and second sensor signals to the control unit using the pair of conductors when power is provided to the first and second sensors, respectively wherein at least one of the sensors senses a plurality of different physiological parameters.

27. The method of claim 26, wherein the first and second sensors are connected in series to the pair of conductors.

28. The method of claim 26, wherein the first and second sensors are connected in parallel to the pair of conductors.

* * * * *